United States Patent [19]

Zarkesh

[11] Patent Number: 5,060,648
[45] Date of Patent: Oct. 29, 1991

[54] BREAST BINDER

[76] Inventor: Shahla Zarkesh, 14144 Saddler River Dr., N. Potomac, Md. 20878

[21] Appl. No.: 595,566

[22] Filed: Oct. 11, 1990

[51] Int. Cl.⁵ .............................................. A61F 7/02
[52] U.S. Cl. .................................. 128/402; 128/379; 450/79; 450/85; 450/89
[58] Field of Search ............. 128/379, 400, 402, 82.1; 450/85, 88, 89, 23, 79, 80, 1

[56] References Cited

U.S. PATENT DOCUMENTS

| | | | |
|---|---|---|---|
| 1,391,936 | 9/1921 | Bosky | 450/89 |
| 1,497,450 | 6/1924 | Kops | 450/79 |
| 2,298,361 | 10/1942 | Freund | 128/402 |
| 2,753,563 | 7/1956 | Blitch | 450/79 |
| 2,762,052 | 9/1956 | Olsen | 450/79 |
| 2,949,115 | 8/1960 | Phillips | 450/80 |
| 3,090,387 | 5/1963 | Hopper | 450/80 |
| 3,500,832 | 3/1970 | Numery | 128/400 |
| 3,995,621 | 12/1976 | Fletcher | 128/402 |

FOREIGN PATENT DOCUMENTS

| | | | |
|---|---|---|---|
| 263041 | 9/1987 | European Pat. Off. | |
| 500270 | 4/1937 | United Kingdom | 128/380 |

*Primary Examiner*—Edward M. Coven
*Assistant Examiner*—Mark S. Graham

[57] ABSTRACT

A breast binder for supporting the breast during breast engorgement. It would be worn after child deliver, basically by mothers who do not intend to breast feed their babies, to help treat the pain caused by breast engorgement.

4 Claims, 1 Drawing Sheet

BREAST BINDER

OBJECTIVES

This invention relates to a very useful, efficient and practical breast binder which helps the patient to feel more comfortable during breast engorgement.

For years physicians have been looking for a device to alleviate the patient's pain during this period. Moreover, in view of the growing reluctance of most physicians to prescribe medication for breast engorgement, this invention provides a simple and natural remedy for this condition.

Although there have been other types of brassieres in the prior art, none have been able to provide so much support to the breasts as this invention does.

The simplicity of the invention is a great inducement for the patient who can put on the binder without any help. It also saves a great deal of time for the hospital nurses. The patient can easily wrap the breast binder around herself, and fasten it as tightly as possible without causing herself discomfort.

The practicality of the invention is one of its main objectives. During breast engorgement, when the use of ice bags is recommended to relieve pain, these can be easily placed in between the overlapping parts of the breast binder. This is easiest way of carrying the ice bags and one of the distinctive features of the invention.

Since support of the breasts and the patient's comfort are the main objects of the present invention, the fabric used has been selected to achieve this aim. It is a mixture of cotton and polyester, firm enough to provide strong support for the breasts, yet soft enough not to hurt the sensitive breasts. It is washable so the patient can reuse it easily during the two-week period of engorgement.

BRIEF DESCRIPTION OF THE DRAWINGS

Some of the objects of the invention having been stated, others will appear as the description proceeds when taken in connection with the drawings, in which.

DETAIL DESCRIPTION OF THE DRAWINGS

Figure 1:
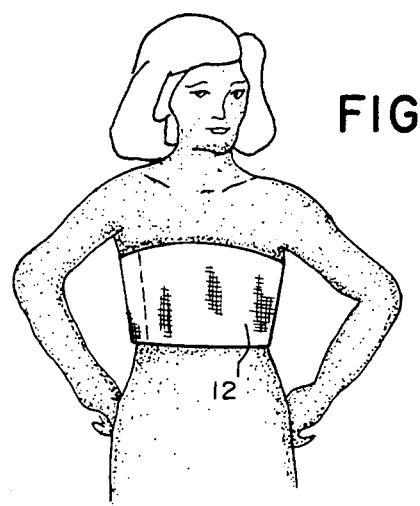
FIG. 1 is a front elevational view of the breast binder as it is worn about the patient's breasts.
Figure 2:
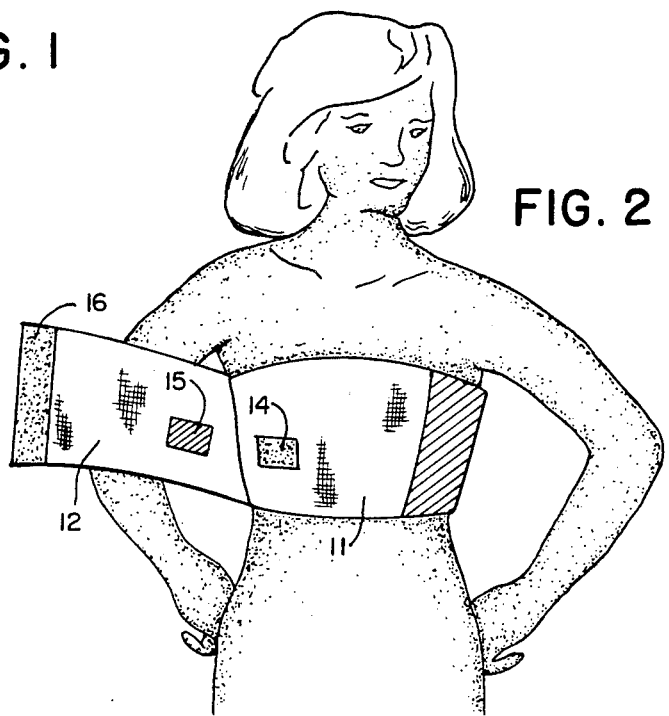
FIG. 2 is an enlarged perspective view of the breast binder. It consists of three panels: panel 10 is the back and panels 11 and 12 are overlapping front parts.

Referring more specifically to the drawings which show the three panels, as shown in FIG. 2, panel 10 is the back part: lengthwise, it is about 2" shorter than the front part, and the upper part is longer than the lower part of the panel [varying according to the size of the binder]. Panel 11 in FIG. 2 is one of the overlapping front parts. In order to cover the breasts completely and provide more support, it is about 2" longer than the back part. It is larger at the top and smaller at the waist. As shown in FIG. 2, VELCRO loop 13 is fixed at the right edge of panel 11. It is 5" wide, which allows the patient to fasten the binder very tightly and adjust it to where she feels comfortable.

Hook VELCRO 14 As shown in FIG. 2 is fixed at the left hand side of panel 11. It is 2 and ½" wide, and 2" long. These are used to fasten the two overlapping parts tightly and thus keep the binder firmly in place.

Figure 3:
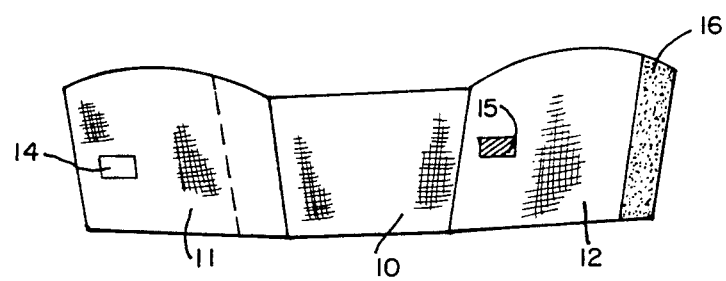
FIG. 3 is an inside view of the breast binder showing where and how the VELCRO is fixed inside panel 12.
Figure 4:
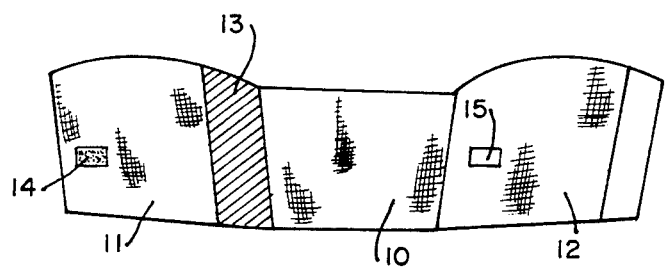
FIG. 4 illustrates how the breast binder is wrapped around the body and fastened at the side.

As seen in FIGS. 2 and 3, panel 12 is the other overlapping front part. The inside of the panel can be seen. In terms of shape, panel 12, is exactly like panel 11. On the right edge of panel 12, is VELCRO hook 16, which is 2" wide and can firmly fasten panel 12 to panel 11 [as seen in FIG. 4]. VELCRO loop 15, is 2 and ½" long and 3 and ½" wide and is fastened to VELCRO 14.

Figure 5:
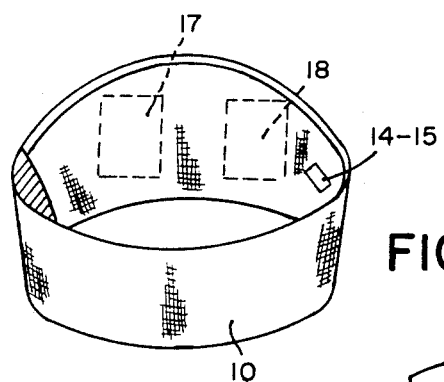
FIG. 5 is an overall view of the breast binder, which shows the back view of the binder as well as the front view with the ice bags placed inside the overlapping parts.

The two VELCROS at the two sides of the overlapping panels help the patient to place the ice bags in between the two overlapping panels, as shown in FIG. 5. Ice bags 17 and 18 are completely secured, and the patient no longer has to carry the bags in her hands. This is a great improvement achieved by this invention.

The two overlapping parts provide a secure place for the ice bags, but they also give the utmost support to the breasts.

It is important to emphasize that the shape of the breast binder has been designed to fit the patient's body very easily. It is larger round the breasts and smaller at the waist. It fits almost every patient and stays firmly in place without any slippage. Thus the binder does not need any straps to keep it in position.

It is understood that the variations from the form of this invention disclosed herein may be made without departure from the spirit and scope of the invention and that the drawings and specification are to be considered merely illustrative rather than limiting.

What is claimed is:

1. A breast binder to protect the breasts during breast engorgement, comprising three attached panels of textile fabric of substantial inherent stability against stretch in use and a fastening means,
    said three panels including a central trapezoidal panel and two similarly shaped adjacent four sided panels including top and bottom sides, the top side of each adjacent panel being convex and of greater length than said bottom side of the respective panel,
    side central panel for placement against the back and said adjacent panels for overlapping the breasts said adjacent panels capable of being fastened with said fastening means in overlapping relationship such that when said adjacent panels overlap they lay on top of one another as substantial mirror images of one another and support the breasts, said adjacent panels adapted to support the ice bags therebetween when said adjacent panels are overlapped.

2. A breast binder according to claim 1, made of a cotton and polyester material which is none stretchable.

3. A breast binder according to claim 1, wherein said fastening means comprises hook and loop fastener at the side of each overlapping panel and hold the two parts firmly together.

4. A method of applying breast binder to protect the breasts during breast engorgement comprising the steps of:
    a: Providing a binder comprising a central trapezoidal panel and two similarly shaped adjacent four sided panels of textile fabric of substantial inherent stability against stretch in use adjacent panels having a top convex side and a shorter bottom side, b: Wrapping the three panels around the patient's body with the two similarly shaped panels overlapping one another in front of the breast area and the central trapezoidal panel being placed against the patient's back, and fastening the binder to itself by fastening means, c: Providing a space between the said overlapping panels, d: Inserting ice bags between the two overlapping panels in front of the breast area.

* * * * *